US008178114B2

(12) United States Patent
Klausen et al.

(10) Patent No.: US 8,178,114 B2
(45) Date of Patent: May 15, 2012

(54) PATCH DEVICE FOR A FRAGRANCE AND METHOD OF USING THE PATCH DEVICE

(75) Inventors: Marius Klausen, Jelling (DK); Roy Lambrecht Lemminger, Juelsminde (DK); Søren Aamand, Egtved (DK); Cristhian Riis, Give (DK)

(73) Assignee: Sentiv ApS, Rungsted Kyst (DK)

( * ) Notice: Subject to any disclaimer, the term of this patent is extended or adjusted under 35 U.S.C. 154(b) by 307 days.

(21) Appl. No.: 12/514,174

(22) PCT Filed: Nov. 9, 2007

(86) PCT No.: PCT/IB2007/054564
§ 371 (c)(1),
(2), (4) Date: May 8, 2009

(87) PCT Pub. No.: WO2008/056338
PCT Pub. Date: May 15, 2008

(65) Prior Publication Data
US 2010/0003294 A1   Jan. 7, 2010

(30) Foreign Application Priority Data

| Nov. 10, 2006 | (DK) | 2006 01476 |
| Jan. 29, 2007 | (DK) | 2007 00141 |
| Mar. 26, 2007 | (DK) | 2007 00465 |
| Jul. 25, 2007 | (DK) | 2007 01090 |

(51) Int. Cl.
*A61K 8/02* (2006.01)
*A61L 9/04* (2006.01)
*A61L 9/01* (2006.01)

(52) U.S. Cl. .............. 424/401; 239/36; 512/1
(58) Field of Classification Search ............ None
See application file for complete search history.

(56) References Cited

U.S. PATENT DOCUMENTS

| 5,846,217 A * | 12/1998 | Beck et al. ............ 604/20 |
| 6,162,457 A | 12/2000 | Martz ............ 424/448 |
| 6,403,186 B1 | 6/2002 | Tararuj et al. ............ 428/40.1 |
| 6,691,872 B1 | 2/2004 | Berman et al. ............ 206/484 |
| 2002/0151236 A1 | 10/2002 | Zolotarsky et al. ............ 442/96 |
| 2002/0160035 A1 * | 10/2002 | Fotinos ............ 424/443 |
| 2005/0256439 A1 * | 11/2005 | Grossman ............ 602/57 |

FOREIGN PATENT DOCUMENTS

| EP | 356 028 A1 | 2/1990 |
| GB | 2 209 532 A | 5/1989 |
| GB | 2 276 321 A | 9/1994 |
| GB | 2 375 482 A | 11/2002 |
| GB | 2375482 A * | 11/2002 |
| JP | 2001 172 153 A | 6/2001 |
| WO | WO 93/00115 A | 1/1993 |
| WO | WO 02/067677 A2 | 9/2002 |
| WO | WO2006/131931 A2 * | 6/2006 |
| WO | WO 2007/028937 A2 | 3/2007 |

OTHER PUBLICATIONS

Cerex Advanced Fabrics (http://www.cerex.com/Zones/Org1/Uploads/products_book.pdf, Accessed Jun. 24, 2011).*
J. Elberling et al., "Contact Dermatitis and Allergy, A Link Between Skin and Airways Regarding Sensitivity to Fragrance Products", British Journal of Dermatology, vol. 151, pp. 1197-1203 (2004).
International Search Report PCT/IB2007/054564 Dated Mar. 27, 2008.

* cited by examiner

*Primary Examiner* — Richard Schnizer
*Assistant Examiner* — Alma Pipic
(74) *Attorney, Agent, or Firm* — Winston & Strawn LLP (57) ABSTRACT

A patch device that includes a backing layer which is a barrier to at least a fragrance, a reservoir layer, which is attached to the backing layer and serves for holding a volume of one or more fragrances, and a cover layer for covering the reservoir layer when filled with fragrance. The cover layer is permeable to vapor from at least one fragrance, which cover layer in a first position of the patch device, in which the reservoir layer is free of fragrance, is situated at least partly offset or dislocated from the reservoir layer, and which cover layer in a second position of use, in which the volume of one or more fragrances has been delivered to the reservoir layer, covers the reservoir layer. Support sheets, which support the backing layer, and a flap part of the cover layer, serve as a tool for applying the flap part into covering relationship to cover or encapsulate the reservoir layer.

17 Claims, 5 Drawing Sheets

PATCH DEVICE FOR A FRAGRANCE AND METHOD OF USING THE PATCH DEVICE

This application is a 371 filing of International Patent Application PCT/IB2007/054564 filed Nov. 9, 2007.

BACKGROUND ART

The present invention relates to a patch device comprising a backing layer which is a barrier to at least fragrance, a reservoir layer, which is attached to the backing layer and serves for holding a volume of one or more fragrances, and a cover layer for covering the reservoir layer when filled with fragrances.

The present invention also relates to a method of using the patch device.

Within the scope of the present invention the term perfume is to be understood as one or more fragrant oils, in particular fragrant ethereal oils, used to give parts of the human body or other objects a long-lasting and pleasant smell. The perfume may contain aroma compounds, fixatives and alcohols for improving emission capabilities.

An allergic contact reaction to perfume is elicited by a hypersensitivity reaction, typically occurring in sensitised individuals within only a few hours after the perfume has been used. The typical allergic perfume contact reactions are characteristically located on the face, hands and arms, which is the skin areas normally subjected to direct application of perfume. The patient may develop symptoms such as disfiguring intense swelling, redness of the affected area, and unpleasant dryness and itching.

The link between eye and airway symptoms triggered by fragrance products, allergic contact sensitisation to topical fragrance products, and hand eczema has also been investigated (Eberling J., Linneberg A., Mosbech H. et al, *British Journal of Dermatology*, 2005; 51(6): 1197-1203. This study established that patients with contact allergy to fragrance products are most likely to develop eye and respiratory symptoms in response to volatile fragrance products, especially patients with underlying atopic disorders such as atopic dermatitis and asthma/reactive airway diseases. It is believed that both allergic reactions, i.e. both contact and airway reactions, have overlapping immunologic pathways and that patients suffering from any one of the allergic reactions should take particular prophylactic attention to avoid both direct application and inhalation of fragrances.

More than 5000 different fragrances are in use today, and the number of fragrances used in a single perfume can be many. Moreover, the recipe of a perfume product is often kept a trade secret making it very difficult for a person to ascertain which fragrance or constituent of the perfume he/she is allergic to. Instead the person must test the perfume with the risk of eliciting an allergic reaction or simply refrain from using perfume or perfume containing products at all.

However most perfume allergy sufferers would prefer to have the option to use perfume at least for a short period without the risk of eliciting an allergic reaction or provoking break out of new associated allergic diseases.

British patent application no. GB 2 375 482 A relates to a single-layered disposable pad that can be pre-impregnated or be impregnated by the user with scents or perfumes. The material of the pad is vapour permeable but not liquid permeable, however the patent application does not provide any indication of how such a pad can be achieved. A pad consisting of a liquid impermeable material cannot be impregnated by the user at the time of use because the liquid perfume cannot be absorbed or penetrate through a material which not is permeable to liquid. The structure described in GB 2375482 is thus not realizable. The impregnated patch is held and encased in a holder, such as a pocket in the clothes or in a wrist band, and cannot be discarded without touching the pad or discarding the entire holder too.

From British patent application GB 2 209 532 A is known a fragrance-emitting article or perfume patch. This known patch includes a fragrance-emitting member being a polyurethane core incorporating a fragrance oil. A surface of the fragrance-emitting member is provided with a pressure sensitive adhesive for adhering the patch to a surface. The fragrance-emitting member may optionally be reinforced by a support layer to improve dimensional stability and strength. Pressure sensitive adhesives dissolve slowly upon contact with liquid. To prevent soluble residues of the pressure sensitive adhesive from sticking to the surface after removal an additional layer may be inserted between the adhesive layer and the polyurethan core to prevent migration of fragrance oil to the adhesive layer. Further, to prevent loss of fragrance during storage the patch is sealed inside an aluminium foil packaging, however during storage a considerable amount of volatile oil evaporates into the package and may be lost the very moment the aluminium foil is opened. A further disadvantage to perfume allergy sufferers is that during wear the fragrance-emitting member has an exposed, touchable wet fragrance emitting side.

International patent application WO 93/00115 discloses a device for controlled release of perfume. The device is prefabricated as a multilayered laminate unit containing an active compound integrated in a reservoir layer, such as hydroxypropyl cellulose gel. A backing barrier layer, which preferably is both liquid and vapour impermeable, is provided on one side of the reservoir layer, and a diffusion rate limiting layer, which allows vapour to pass through, is provided on the other side of the reservoir layer. An adhesive layer for adhering the device to the skin is provided on the surface of the impermeable membrane layer. A peeling layer, which is impermeable to the perfume, is placed topmost of the laminate for storage. In order to learn the smell of the fragrance or test the perfume the user needs to break the packaging. Furthermore, it is not possible for the user to use a perfume of her/his own choice.

SUMMARY OF THE INVENTION

In a first aspect according to the present invention is provided a patch device of the kind mentioned in the opening paragraph that can receive a volume of a perfume of the users own choice and emit the perfume under minimum allergic risk conditions.

In a second aspect according to the present invention is provided a patch device of the kind mentioned in the opening paragraph with a closable perfume reservoir.

In a third aspect according to the present invention is provided a patch device of the kind mentioned in the opening paragraph that can be applied to a surface and discarded without touching the perfume in the reservoir layer.

The novel and unique whereby this is achieved according to the present invention is the fact that the cover layer is permeable to vapour from at least one fragrance, which cover layer in a first position of the patch device, in which the reservoir layer is free of fragrance, is situated at least partly offset or dislocated from the reservoir layer, and which cover layer in a second position of use, in which the volume of one or more fragrances has been delivered to the reservoir layer, covers the reservoir layer.

The patch device advantageously provides perfume allergy sufferer with the possibility of wearing conventional perfumes of personal choice without prior knowledge of the composition of the perfumes. The one or more fragrances, such as a perfume, are encapsulated between the backing layer and the cover layer during use and no physical contact with the perfume is involved during delivery of the perfume to the reservoir layer, coverage of the perfume-filled reservoir layer with the cover layer and during wear of the closed patch device. The cover layer is in a simple manner arranged to cover the reservoir layer, e.g. by simple pulling the cover layer across the reservoir layer. Due to the flexible nature of the material of the cover layer, the cover layer almost by itself conforms around and encapsulates the reservoir layer to prevent liquid escape. Furthermore, the cover layer constitutes a barrier to dirt and moisture from the environment. Only vapour permeates from the reservoir layer through the cover layer and the closed patch device constitutes a safe solution to perfume allergy sufferers who miss the possibility of wearing e.g. conventional perfumes. The patch device may be used during any expedient period to thereby minimize exposure to perfume and elicit associated airway diseases or other kinds of sequela. The patch device can be discarded whenever desired to immediately get completely rid of any exposure to the allergy-causing agent without needing to wash the skin or take a shower, which options not always is immediate accessible.

It is preferred, that the area of the reservoir layer is smaller than the area of the backing layer to thereby define a free edge area of the backing layer with no reservoir layer coverage. This free edge may advantageously serve for joining with a corresponding edge area of the flexible cover layer. The flexible cover layer may be adhesive in itself or may be coated with an adhesive at least along the edge area to facilitate firm and secure joining of the opposing, contacting edge areas. Alternatively the edge area of the backing layer is coated with a suitable adhesive selected to bond to the cover layer. Preferably, the edge areas are joined to each other to a degree in which the joint constitutes a liquid seal.

In a simple embodiment according to the present invention the cover layer can be divided along a fold line into a flap part for covering the reservoir layer and an attachment part secured to a section of the edge area of the backing layer. When the attachment part is fixed on the edge area the flap part can easily be pivoted or folded about the fold line to engage, cover, enclose and/or encapsulate the reservoir layer. If the backing layer is provided with a detachable or non-detachable grasping flap subsequent application of the closed fragrance-filled patch device are facilitated.

A surface facing side of the backing layer may be provided with an adhesive or an adhesive layer to allow easy adhesion to e.g. the skin of the user. The preferred adhesives for skin application are tested hypoallergenic but for application on other surfaces the adhesive can be of any suitable kind.

In the preferred embodiment according to the present invention the patch device may further comprise a first support sheet on top of which the backing layer and the flap part are releasable attached next to each other in the first position of the cover layer. The support sheet enlarges the area for holding the entire device and provides a finger grip distanced from the perfume application spot, i.e. the reservoir layer. The risk of excessive perfume delivery and contact with the excess is thus substantially reduced. When the cover layer is to be brought into the second position the user can easily release the flap part from the first support sheet by pulling the flexible cover layer laterally across the reservoir layer using the fingertips or any other suitable means. Finally the closed patch device is released from the first support sheet.

To prevent the backing layer from releasing from the first support sheet before the flap part releases the attachment force between the first support sheet and the backing layer may preferably be greater than the attachment force between the first support sheet and the flap part. This arrangement also serves for preventing unintentional crumpling up of the thin, flexible cover layer which crumpling up would damage the safe functionality of the device.

The cover layer can in an especially easy and safe routine procedure be folded into the second position if the patch device further is provided with a second support sheet, which in the first position of the cover layer is releasable attached to at least the side of the flap part opposite the first support sheet, which second support sheet in the first position of the cover layer at least partly overlaps the first support sheet.

When the cover layer is to be moved to the second position the user may avoid exposure of the fingertips to the fragrances hold in the reservoir layer by grasping a free end of the second support sheet instead of just grasping the cover layer itself, and pulling the second support sheet apart from the first support sheet thereby folding the cover layer in over the reservoir layer. The second support sheet is used as a pulling and folding tool for gradually releasing the cover layer from both the first support sheet and the second support sheet, and the first support sheet is used as a counteract or pulling tool in the opposite direction of the pulling direction of the second support sheet.

To prevent the second support sheet and first support sheet from unintentional displacement in relation to each other before the cover layer shall be moved to its second position, the first support sheet and the second support sheet may be releasable secured to each other using any appropriate securing means. Such a means could e.g. be the adhesive provided at the edge section of the backing layer which is utilized for adhesion of the cover layer to the backing layer in the second position of the cover layer, however any easy breakable spot gluing connecting the two support sheets could quite as well prevent displacement of the two support sheets in relation to each other before it in fact is intended. The overlapping relationship of the support layers furthermore may serve to protect the delicate permeability properties of the cover layer.

The second support sheet advantageously has a traversing fragrance charging opening located above the reservoir layer in the first position of the cover layer for easy and directional delivery of the fragrance.

If the cover layer is elastic it will by itself conform around the outline and topography of the reservoir layer.

Optionally release liners are inserted between any of the backing layer and the first support sheet, the cover layer and the first support sheet, and the cover layer and the second support sheet. Any number and kind of appropriate intermediate layers may be inserted within the scope of the present invention provided the basic layers, i.e. the backing layer, the reservoir layer and the cover layers and its functions are preserved.

As an example a first release liner or intermediate layer may be inserted between the backing layer and the first support sheet may serve to partly protect the skin adhesive on the backing layer so that the final attachment capability to the skin is not in anyway damaged by the intermediate attachment to the first support sheet.

Another example is a second release liner or intermediate layer inserted between the cover layer and the first support sheet to provide stiffness to the cover layer thereby assisting in preventing crumpling of the cover layer during both storage and when the cover layer is pulled into its second position. In case a second release liner is inserted between the cover layer and the first support sheet the attachment force between the second release liner and the cover layer must be smaller than the attachment force between the first support sheet and the backing layer, or in case a first release liner is provided, between the first support sheet and the backing layer first release liner.

Yet another example is a third release liner or intermediate layer inserted between the cover layer and the second support sheet. The third release liner serves in the same manner as the second release liner for providing stiffness and prevent crumpling of the cover layer.

The release liners or intermediate layers are optional and provided optionally provided with non-stick adhesives on one or both sides according to requirements.

The method of using the patch device according to the present invention as described above comprises in a first step and in the first position of the cover layer applying a self-elected volume of a self-elected fragrance to a dry reservoir layer, in a second step moving the flap part to the second position to cover and enclose the fragrance containing reservoir layer, and in a third step detachable applying the patch device to a surface for emitting fragrance through the permeable cover layer for a self-elected period of time.

When using the preferred embodiment for at patch device with support sheets according to the present invention the first step comprises applying the fragrance through the traversing fragrance charging opening of the second support sheet, the second step comprises moving the first and the second support sheet apart thereby bringing the flap part along in over the reservoir layer while in the same manoeuvre releasing the flap part from its connection to the second support sheet, and the third step comprises releasing the backing layer from its connection to the first support sheet and applying the patch device to a surface. If release liners or intermediate layers are used the adhesive connections with the support sheets may alternatively be triggered when the two support sheets are taken apart by pulling them in opposite directions.

BRIEF DESCRIPTION OF THE DRAWINGS

The invention will be explained in greater detail below, describing only exemplary embodiments with reference to the drawing, in which.

DETAILED DESCRIPTION OF THE PREFERRED EMBODIMENTS

In the following the invention is shown and described by way of exemplary embodiments for patch devices and a method of using the patch devices are illustrated.

The geometric shape of most of the illustrated components of the patch device are oval or circular, however within the scope of the present invention any geometric shape is intended and foreseen. Accordingly, the geometric shape could quite as well be squared.

In the present application and accompanying drawing the terms backing layer, reservoir layer and cover layer are described and shown as single layer structures. Within the scope of the present invention it is to be understood that any of these layers may be composed of more than one layer to obtain the desired properties of each respective layer, i.e. be able to prevent permeation of fragrance to the subjacent surface, e.g. a skin surface to which the patch device is attached, be able to absorb and retain a volume of liquid, e.g. a liquid perfume, and be able to cover, preferably encapsulate completely, a reservoir layer filled with fragrances, respectively.

Figure 1:
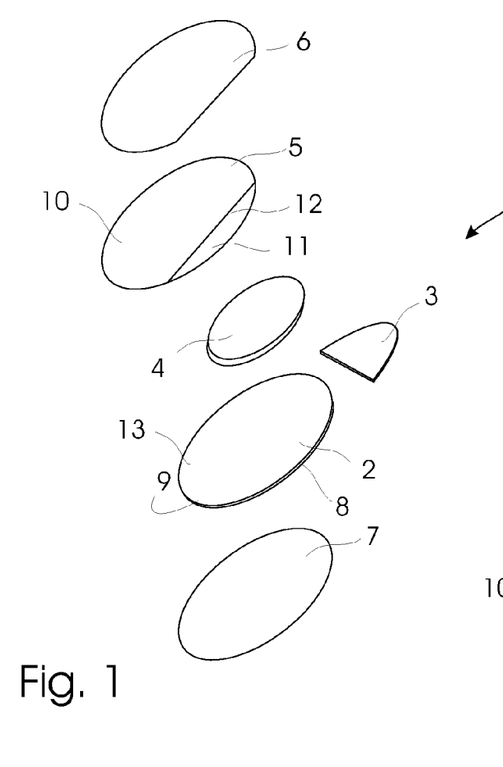
FIG. 1 shows an exploded view, seen in perspective, of a first embodiment for a patch device according to the present invention.

FIG. 1 shows an exploded view, seen in perspective, of a first simple embodiment for a patch device 1 according to the present invention. The patch device 1 consist of a backing layer 2, a grasping flap 3, a reservoir layer 4, a cover layer 5, a third release liner 6 for protecting and stiffening the cover layer 5, and a first release liner 7 for protecting an adhesive 8 on a skin facing side 9 of the backing layer 2. The cover layer 5 has a flap part 10 and an attachment part 11 for securing the cover layer 5 to the backing layer 2. The flap part 10 merges into the attachment part 11 via a fold line 12. The backing layer 5 has an area, which is larger than the area of the reservoir layer to define a circumferential edge area 13, which may or may not be provided with an adhesive (not shown) for firmly adhering the cover layer 5 to the backing layer 2 to encapsulate a perfume delivered to and absorbed by the reservoir layer 2.

Figure 2:
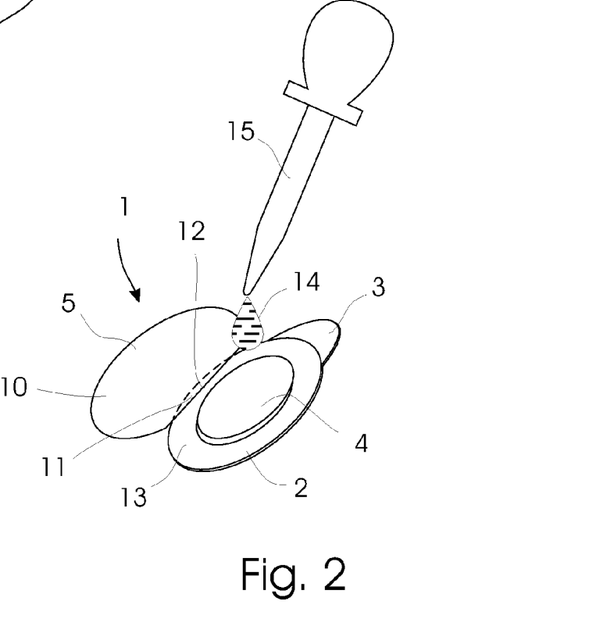
FIG. 2 shows the same in assembled state in the first position of the cover layer.

FIG. 2 shows the patch device 1 with the cover layer 5 in the first position wherein the flap part 10 is folded along fold line 12 to an offset position wherein the flap part 10 is situated next to the backing layer 2, side by side. The attachment part 11 overlaps a section of the edge area 13 of the backing layer 2 and is firmly attached to this section, e.g. by means of glue. The reservoir layer 4, which is fixed and secured to the backing layer 2 substantially concentric with said backing layer 2, is ready to receive a drop of perfume 14, which may be delivered by any appropriate dispenser means, e.g. a pipette 15 as shown in FIG. 2. The various firmly joined components may be glued together. It is important that the patch device remains intact during use. Since the ethereal oils of perfumes often are dissolved in alcohol the preferred glue is selected among glues, which do not dissolve upon contact with alcohol. Alternative appropriate joining means such as welding can be used instead of glue.

Figure 3:
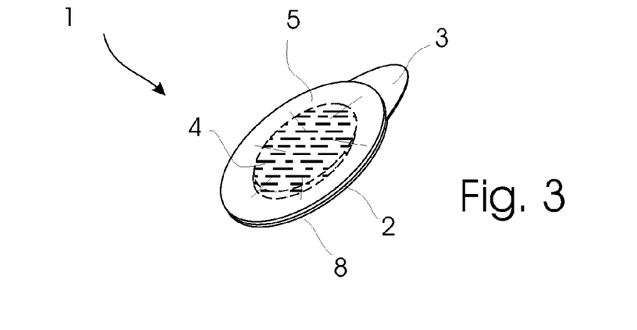
FIG. 3 shows the same in assembled state in the second position of the cover layer.

FIG. 3 show the first embodiment of the patch device 1 in the second position in which the flap part 10 of the cover layer 5 is folded about the folding line 12, indicated in FIG. 2, to cover the perfume 14 containing reservoir layer 4. Folding may take place by holding the patch device 1 in one hand and pulling the cover layer 5 in over the reservoir layer 4 using the release liner 6 as a pulling tool.

Figure 4:
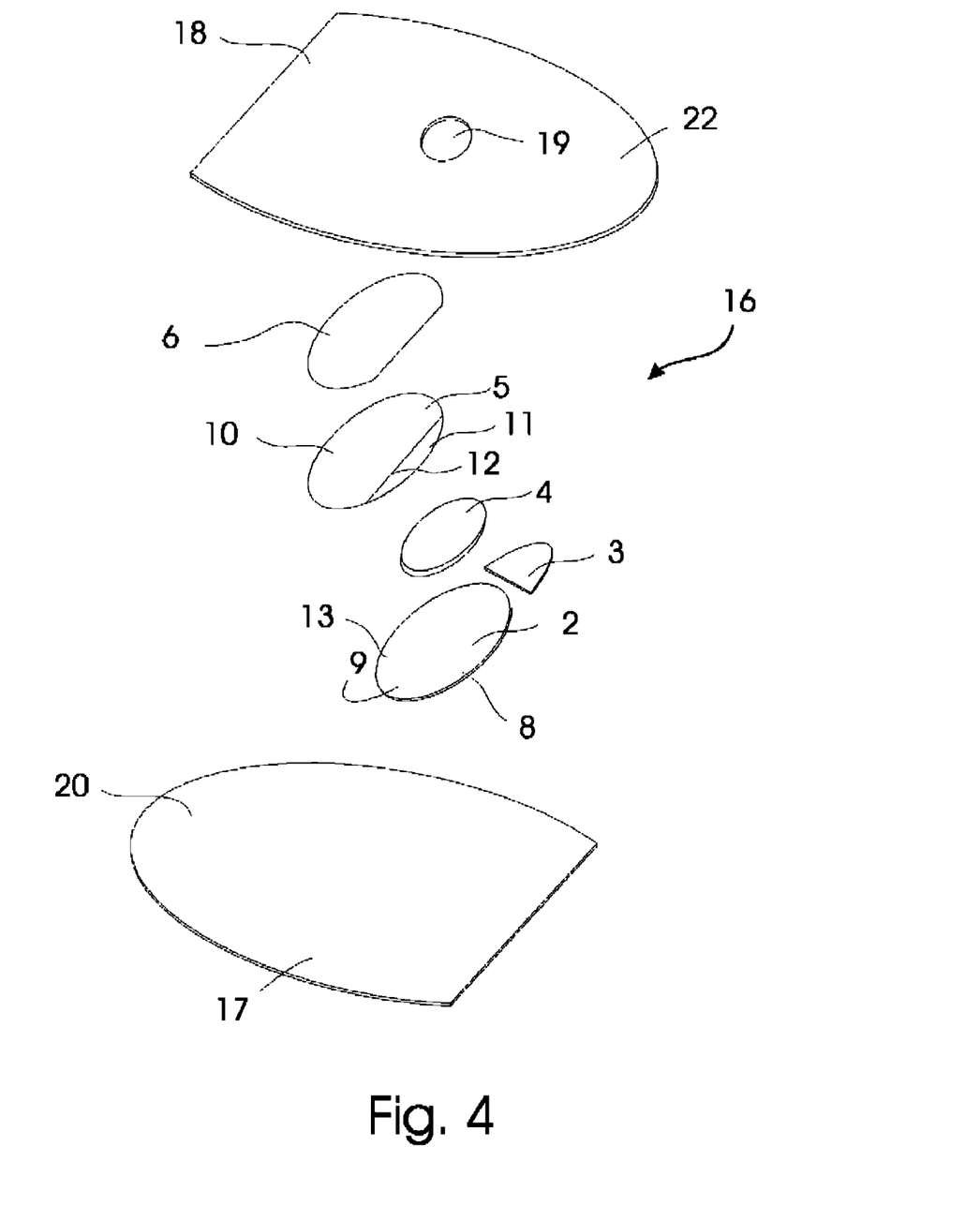
FIG. 4 shows an exploded view, seen in perspective, of a second embodiment for a patch device according to the present invention.

FIG. 4 shows an exploded view, seen in perspective, of a second embodiment for a patch device 16 according to the present invention. The second embodiment for a patch device 16 corresponds substantially to the first embodiment for a patch device 1, and for like parts same reference numerals are used. The second embodiment is shown not to include the first release liner 7, but such a release liner is optional.

The patch device 16 includes as additional components a first support sheet 17 and a second support sheet 18 with a traversing fragrance charging opening 19 for delivering a perfume 14 to the reservoir layer 4.

Figure 5:
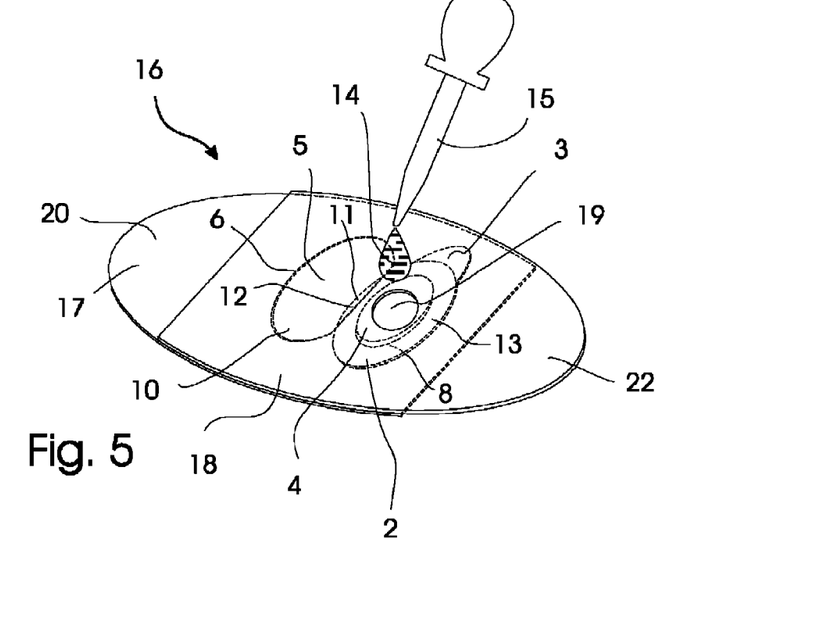
FIG. 5 shows the same in assembled state in the first position of the cover layer.

The perspective view of FIG. 5 substantially include the perspective view of FIG. 2 and illustrates how the first support sheet 17 and the second support sheet 18 are arranged on both sides of the combined backing layer 2, reservoir layer 4, and cover layer 5 in the first position of the cover layer 5 for the second embodiment of a patch device 16. By means of the adhesive 8 of the backing layer 2 said backing layer 2 is releasable joined to the first support sheet 17 side by side with the flap part 10 of the cover layer 2. In the case shown the flap part 10 is not adhered to the first support sheet 17 but is releasable adhered to the release liner 6, which in turn is adhered firmly to the second support sheet 18. The release liner 6 provides the flap part 10 with stiffness and dimensional stability during storage of the patch device 16 in the first position of the cover layer 5.

Figure 6:
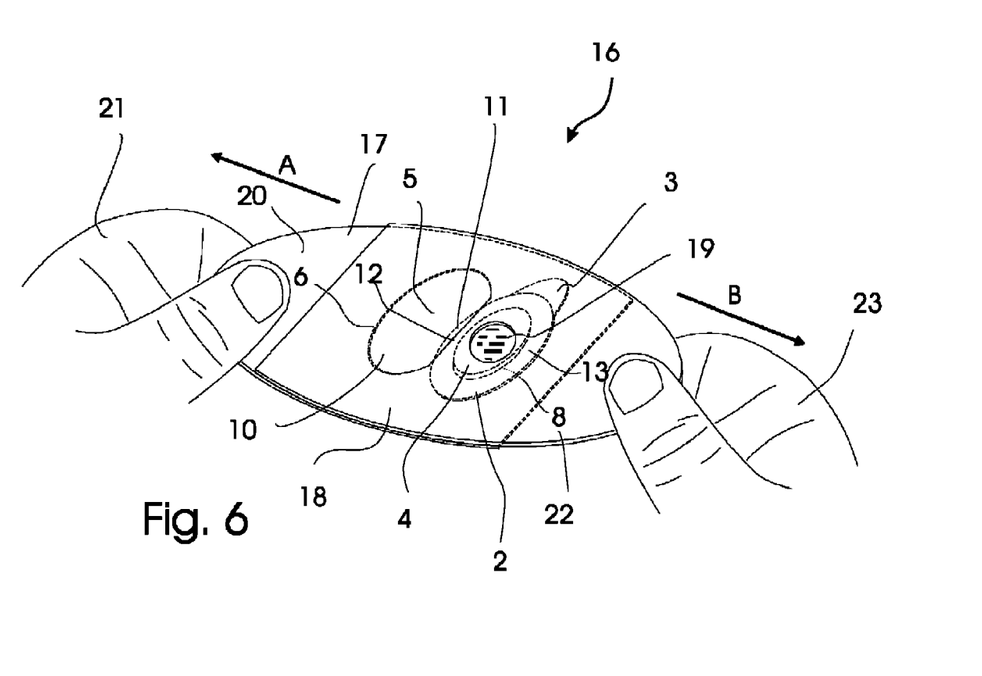
FIGS. 6 and 7 shows the same during a second step in which the cover layer is moved from the first position to the second position.
Figure 7:
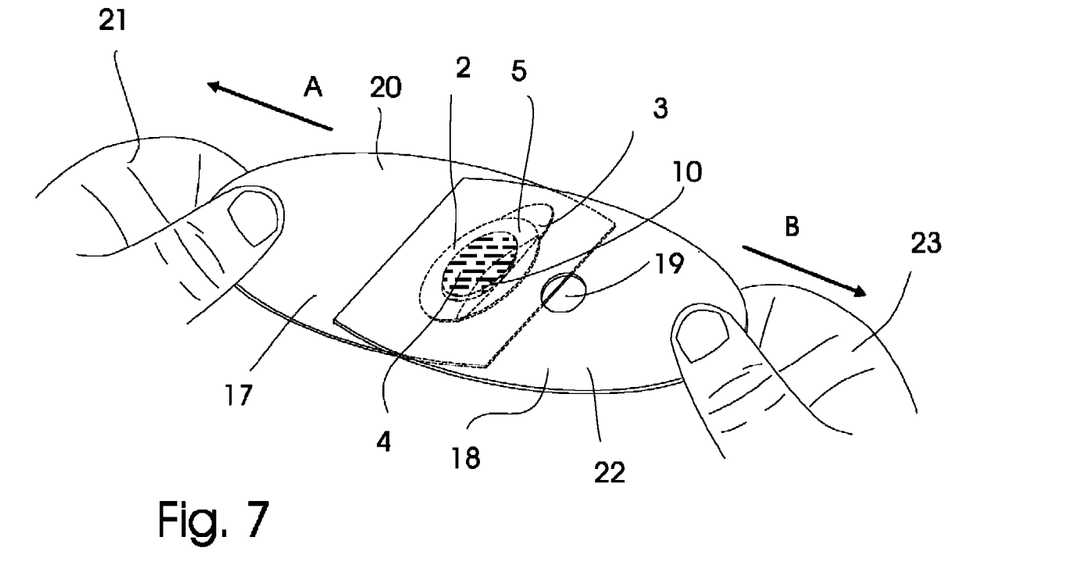

The second method steps of transferring the flap part 10 of the cover layer 5 to the second position in which the cover layer 5 is positioned on top of the combined reservoir layer 4 and backing layer 2 is illustrated in FIGS. 6 and 7.

The free end 20 of the first support sheet 17 are hold between the left hand fingers 21, and the free end 22 of the second support sheet 18 are hold between the right hand fingers 23. Then, as indicated with the opposing arrows A and B, during the second step the first support sheet 17 and the second support sheet 18 are carefully pulled apart, and the flap part 10 is released from the second support sheet 18. As seen best in FIG. 7, by pulling the second sheet 18 in the direction of the arrow B while holding back the first support sheet 17 in the direction indicated with the arrow B, the side of the flap part 10 facing the second support sheet 18 is folded or rolled into contact with the reservoir layer 4 and adhered to the edge area 13 of the backing layer 2. The adhesion between the edge area 13 and the flap part 10 may be made stronger by manually pressing on opposing exterior sides of the respective support sheets 17,18 alone the edge area 13.

Figure 8:
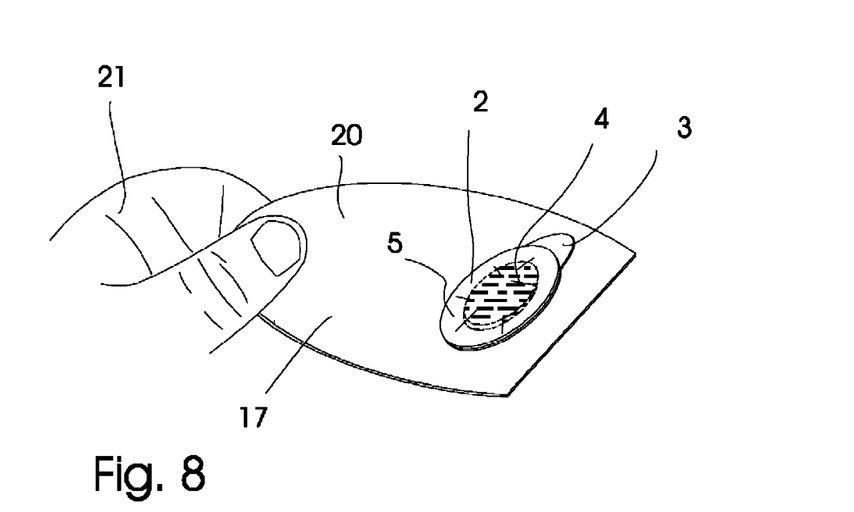
FIG. 8 shows the cover layer in the second position and the backing layer attached to the first support sheet.

The pulling apart action is continued until the cover layer 5 covers the reservoir layer 4 and is completely set free of the second support sheet 18, as illustrated in FIG. 8.

Figure 9:
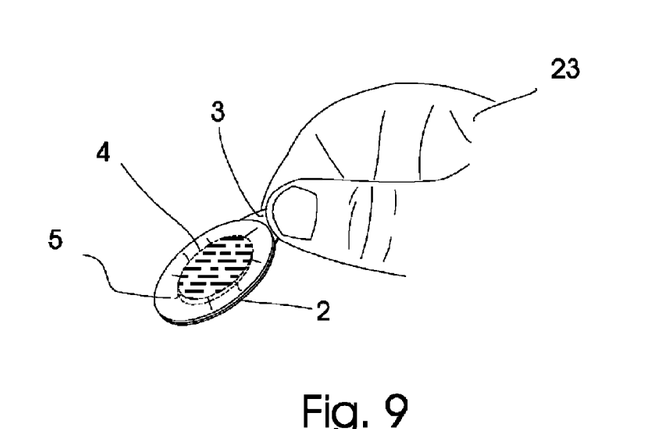
FIG. 9 shows the patch released from the first support sheet.

The patch 2,3,4,5 is now released from the first support sheet 17 as seen in FIG. 9 and ready to be transferred to an application surface.

Figure 10:
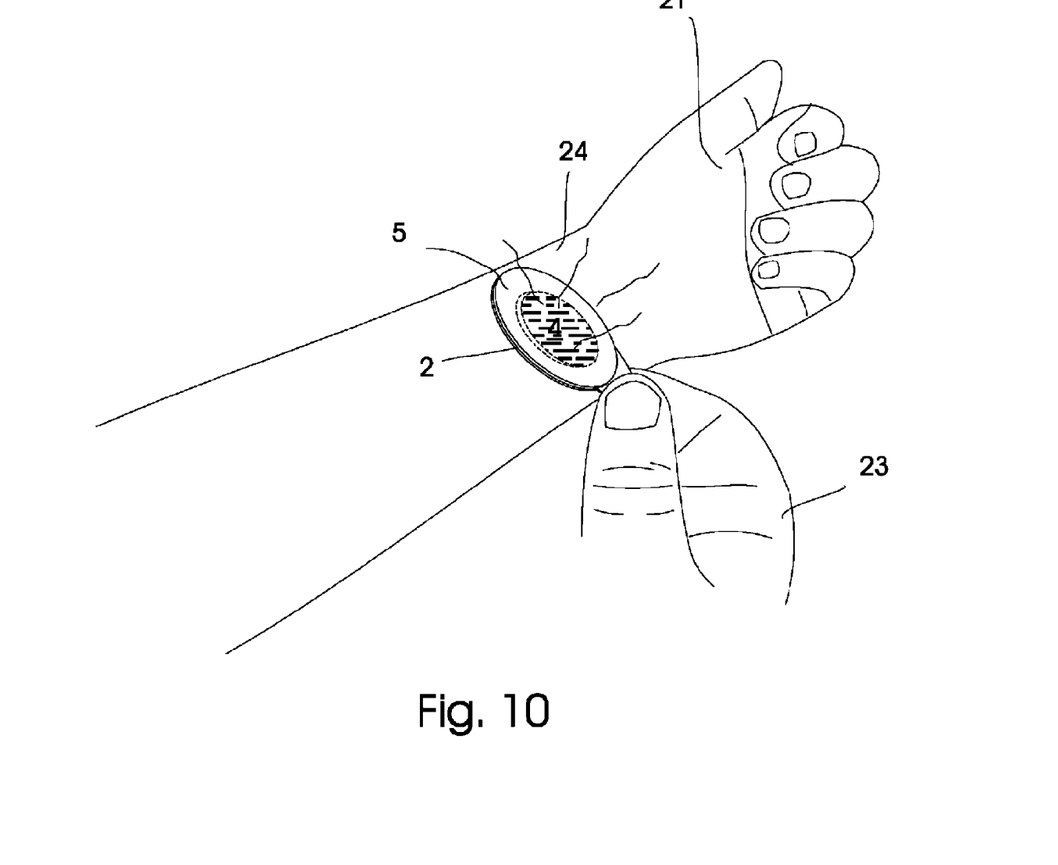
FIG. 10 shows the patch mounted on the wrist of a persons left arm.

As illustrated in FIG. 10 a suitable surface is the wrist 24 of a person suffering from perfume allergy, however other users and surfaces are intended within the scope of the present invention.

Within the scope of the present invention various materials can be used for the components of the patch devices 1;16.

The material for the reservoir layer 4 must be selected to absorb and hold a volume of perfume. Sponge-like materials and non-wovens are examples of suitable materials.

The material for the backing layer is selected to be a barrier layer allowing no perfume content to penetrate through it. Thin metal coated foils obtained by sputter coating a carrier sheet or other material having a very dense molecular structure may be used.

The backing layer has an adhesive on the surface contacting face, and for use at a skin surface the adhesive is chosen among adhesives known not to elicit skin allergy, e.g. a hydrocolloid.

The cover layer may advantageously be chosen as a flexible membrane, preferably a low density membrane layer, which is selectively permeable to one or more kinds of fragrance vapour molecules. A suitable cover and membrane layer material are e.g. polyethylene, preferably a low density polyethylene. Also the polyethylene laminate membrane disclosed in U.S. Pat. No. 5,804,264 may be used.

The support sheets may advantageously be made transparent to allow inspection during transferring the cover layer to the second position. The support sheets may also be coloured and user instructions may be printed on them.

The preferred materials for the structural patch device components are easy to recycle and do not release hazardous compounds when being processed or recycled to thereby reducing impact on the environment.

What is claimed is:

1. A patch device for emitting one or more fragrance(s), comprising:
    a backing layer which is a barrier at least to the fragrance(s) carried by the patch device, a reservoir layer which is attached to the backing layer for absorbing and retaining a volume of one or more fragrances, and
    a cover layer for covering the reservoir layer when filled with the one or more fragrance(s), wherein the cover layer (a) is permeable to vapour from at least one fragrance, (b) is at least partly laterally offset or dislocated from the reservoir layer in a first position of the patch device in a location where the reservoir layer is free of fragrance, and (c) covers the reservoir layer in a second position, in which the volume of one or more fragrances has been delivered to the reservoir layer, wherein the cover layer is movable between the first and the second positions.

2. The patch device of claim 1, wherein the reservoir layer has a size that is smaller than that of the backing layer, thereby defining a free edge area of the backing layer that does not contact the reservoir layer.

3. The patch device of claim 2, wherein the cover layer is divided along a fold line into a cover layer flap for covering the reservoir layer in the second position and an attachment part secured to a section of the edge area of the backing layer in the first position.

4. The patch device of claim 1, which further comprises a detachable or non-detachable grasping flap on the backing layer.

5. The patch device of claim 1, which further comprises an adhesive on a surface facing side of the backing layer.

6. The patch device of claim 3, which further comprises a first support sheet on top of which the backing layer and the cover layer flap are releasably attached next to each other in the first position of the cover layer.

7. The patch device of claim 6, wherein the first support sheet and the backing layer are joined by an attachment force that is greater than that between the first support sheet and the flap.

8. The patch device of claim 6, which further comprises a second support sheet, which in the first position of the cover layer is releasably attached to the side of the cover layer flap opposite the first support sheet, wherein the second support sheet at least partly overlaps the first support sheet.

9. The patch device of claim 8, wherein the second support sheet has a fragrance charging opening located above the reservoir layer in the first position of the cover layer.

10. The patch device of claim 8, which further comprises release liners or intermediate layers positioned between the backing layer and the first support sheet, the cover layer and the first support sheet, or the cover layer and the second support sheet.

11. The patch device of claim 1, wherein the cover layer is elastic.

12. The patch device of claim 1, wherein the fragrance is a perfume.

13. A method of emitting a fragrance, which comprises:
providing a patch device according to claim 9;
in a first step and in the first position of the cover layer applying a self-elected volume of the one or more fragrance(s) to the reservoir layer; and
in a further step detachably applying the patch device to a surface for emitting the fragrance through the vapour permeable cover layer.

14. The method of claim 13, wherein the patch device further comprises a detachable or non-detachable grasping flap on the backing layer and the method further comprises in a second step moving the cover layer flap laterally towards the second position to cover and enclose the fragrance containing reservoir layer.

15. The method of claim 14, wherein:
the first step comprises applying the fragrance through the fragrance charging opening of the second support sheet,
the second step comprises moving the first support sheet and the second support sheet apart thereby bringing the cover layer flap over the fragrance filled reservoir layer and releasing the cover layer flap from its attachment to the second support sheet, and
the third step comprises releasing the backing layer from its attachment to the first support sheet before applying the patch device to a surface.

16. The patch device of claim 5, wherein the adhesive is a pressure sensitive adhesive and is hypoallergenic.

17. A method of emitting one or more fragrance(s), which comprises:
providing a patch device according to claim 1;
in a first step and in the first position of the cover layer applying a self-elected volume of the one or more fragrances to the reservoir layer; and
in a further step detachably applying the patch device to a surface for emitting the fragrance through the vapour permeable cover layer.

* * * * *

UNITED STATES PATENT AND TRADEMARK OFFICE
CERTIFICATE OF CORRECTION

PATENT NO. : 8,178,114 B2
APPLICATION NO. : 12/514174
DATED : May 15, 2012
INVENTOR(S) : Klausen et al.

It is certified that error appears in the above-identified patent and that said Letters Patent is hereby corrected as shown below:

Column 8:
Line 24 (claim 1, line 4), after "device", start a new paragraph with "a reservoir layer which is".
Line 26 (claim 1, line 6), change "fragrances" to -- fragrance(s) --.
Line 27 (claim 1, line 7), start a new subparagraph to be in line with the preceding subparagraphs.
Line 29 (claim 1, line 9), change "vapour" to -- vapor --.
Claim 1 will correctly appear as follows:
    1. A patch device for emitting one or more fragrance(s), comprising:
    a backing layer which is a barrier at least to the fragrance(s) carried by the patch device,
    a reservoir layer which is attached to the backing layer for absorbing and retaining a volume
        of one or more fragrance(s), and
    a cover layer for covering the reservoir layer when filled with the one or more fragrance(s),
    wherein the cover layer (a) is permeable to vapor from at least one fragrance, (b) is at least
    partly laterally offset or dislocated from the reservoir layer in a first position of the patch
    device in a location where the reservoir layer is free of fragrance, and (c) covers the
    reservoir layer in a second position, in which the volume of one or more fragrances has
    been delivered to the reservoir layer, wherein the cover layer is movable between the first
    and the second positions.

Line 58 (claim 7, line 3), after "and the", insert -- cover layer --.

Column 9:
Line 17 (claim 13, line 7), change "vapour" to -- vapor --.

Column 10:
Line 21 (claim 17, line 8), change "vapour" to -- vapor --.

Signed and Sealed this
Twenty-sixth Day of June, 2012

David J. Kappos
*Director of the United States Patent and Trademark Office*